United States Patent

Hunt

Patent Number: 5,431,066
Date of Patent: Jul. 11, 1995

[54] DEVICE FOR PREPARING SAMPLES OF POWDERED METALS FOR ANALYSIS

[75] Inventor: Thomas J. Hunt, Peekskill, N.Y.

[73] Assignee: Materials Research Corporation, Orangeburg, N.Y.

[21] Appl. No.: 234,235

[22] Filed: Apr. 28, 1994

[51] Int. Cl.$^6$ .............................................. G01N 1/00
[52] U.S. Cl. ...................................... 73/863; 73/19.07
[58] Field of Search .................... 73/863, 19.7; 425/78, 425/110, 112, 117, 127

[56] References Cited

U.S. PATENT DOCUMENTS

| | | | |
|---|---|---|---|
| 2,883,703 | 4/1959 | Frank | 425/78 |
| 3,053,075 | 9/1962 | Lipson et al. | 73/19.07 |
| 4,562,026 | 12/1985 | Mosher | 425/127 |
| 4,719,187 | 1/1988 | Bardhan et al. | 501/97 |

*Primary Examiner*—Robert Raevis
*Attorney, Agent, or Firm*—Wood, Herron & Evans

[57] ABSTRACT

A device for the preparation of powdered metal samples for oxygen analysis includes a mold with a central cavity accessible through a tapered throat region on the top of the mold. A tin foil sheet is placed in the tapered throat region and pressed into the cavity and thereby formed into a generally cup shaped configuration. A measured amount of the powdered metal is poured into the cup shaped tin foil within the cavity of the mold. A tweezers is used to fold the tin foil over thereby encapsulating the powdered metal within the foil. The sample is then tamped to form a tightly packed specimen for analysis. The diameter of the cavity corresponds to the diameter of the crucible in the oxygen analyzer to thereby consistently provide an appropriately sized powdered metal sample with a minimum of operator time. The mold is preferably constructed in two pieces with an upper portion removable from a base portion. After the tin foil is folded to encapsulate the powdered metal sample within the cavity of the mold, the upper portion is removed from the base to expose the sample for removal by the operator with the tweezers from the base.

27 Claims, 1 Drawing Sheet

U.S. Patent  July 11, 1995  5,431,066
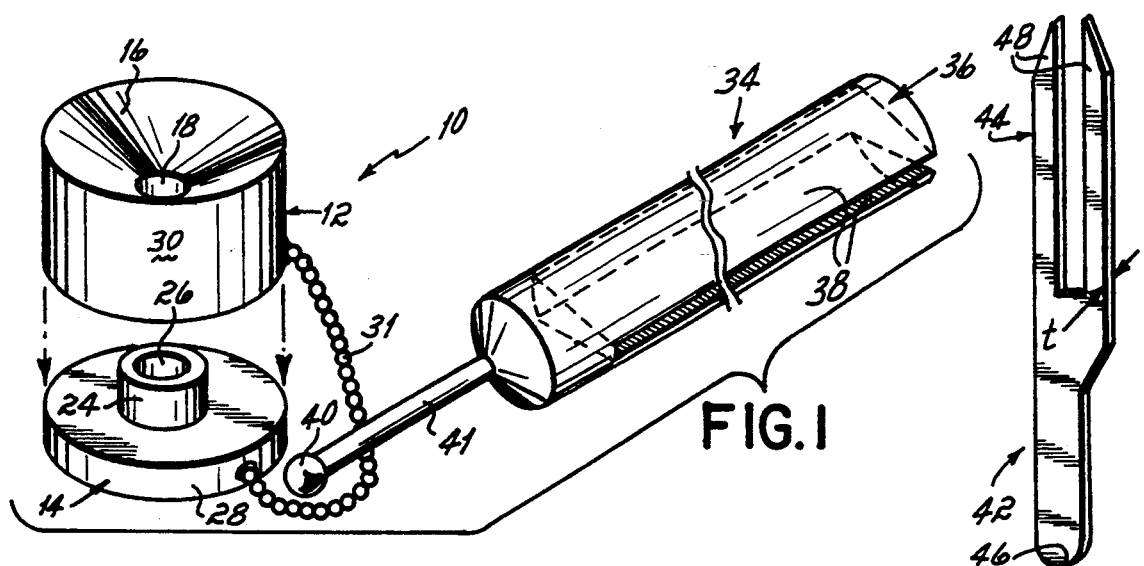
FIG. 1
FIG. 2
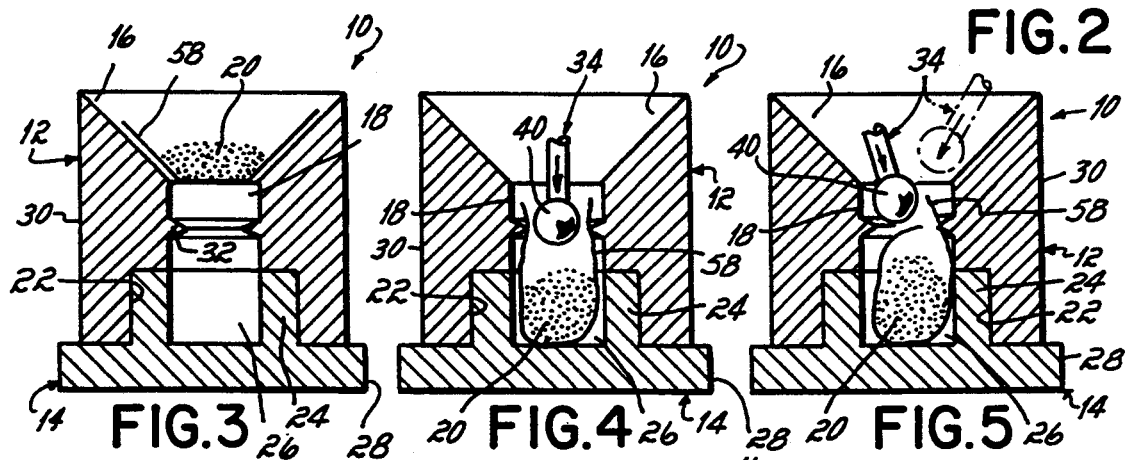
FIG. 3  FIG. 4  FIG. 5
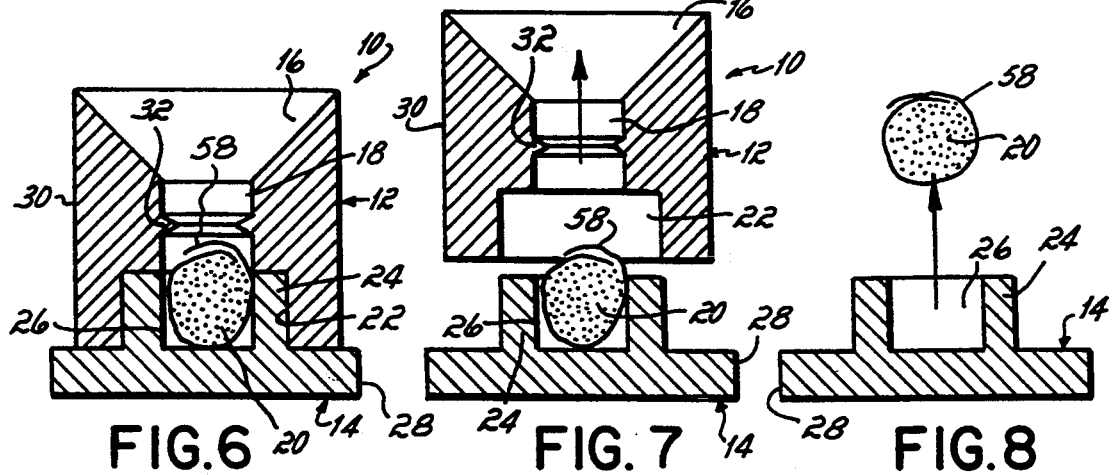
FIG. 6  FIG. 7  FIG. 8
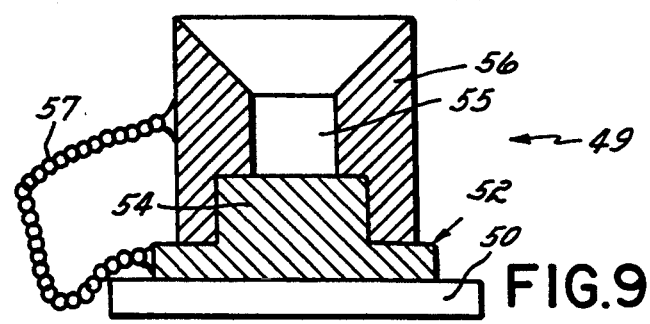
FIG. 9

DEVICE FOR PREPARING SAMPLES OF POWDERED METALS FOR ANALYSIS

BACKGROUND OF THE INVENTION

This invention relates to the field of powdered metallurgy, and more particularly, to the preparation of samples of powdered metals for oxygen analysis.

In the field of powdered metallurgy, it is often necessary to provide a sample of a powdered metal for oxygen analysis to determine the oxygen content therein. This analysis is accomplished by heating a sample of the powdered metal, for example titanium or tungsten, in a crucible and taking a background reading of the oxygen content in the crucible. A standard reference for oxygen analysis acceptability is approximately 600 to 1300 parts per million.

A typical procedure for the preparation of a powdered metal sample for oxygen analysis is to encapsulate a measured amount of the powder in a tin foil packet. In that powdered metals tend to oxidize, the encapsulation procedure must be done in an inert atmosphere such as argon. To achieve the inert atmosphere, the sample is typically collected and packaged in the tin foil in a glove box. The glove box includes a pair of gloves, typically rubberized and often bulky, which the operator uses to encapsulate the sample in the foil within the glove box.

The samples deposited into the crucible of the analyzer for oxygen analysis should ideally be well formed and of a uniform size in order to yield consistently accurate results. Typically, a 0.2 gram sample of the powdered metal is required for the oxygen analysis. Due to the nature of the gloves and the small scale of the samples, the operator usually has an extremely difficult time handling the foil and powdered metal within the glove box, The bulky gloves detrimentally affect the manual dexterity of the operator. As a result, powdered metal samples for oxygen analysis which are packaged in the glove box are often of varying sizes and shapes.

In addition to the problem of non-uniformity of package sizes prepared in a glove box, the tin foil sheet used to encapsulate the sample is typically very thin, approximately 0.0005 of an inch thick. Therefore, the foil easily tears and the packages prepared in the glove box are easily damaged allowing the powdered metal to leak from the package, thereby resulting in a non-uniform sample weight and inconsistent test results.

These and other difficulties encountered in handling and manipulating very small samples of powdered metal while operating in a glove box result in a very tedious and time consuming process for the operator. Numerous samples are often required for repeated analysis. A typical preparation time for a powdered metal sample in a glove box is approximately one minute. However, even a careful and diligent operator can expect as much as an 80% rejection rate of samples prepared in a glove box due to irregularly sized, shaped, damaged and/or leaking sample packets.

SUMMARY OF THE INVENTION

A primary objective of this invention has been to provide a device to reduce variations in the preparation of powdered metal samples for oxygen analysis and thereby achieve more consistent and reliable results.

A further objective has been to provide such a device which requires minimal operator time to prepare the samples.

A still further objective has been to provide such a device which can be easily operated within the confines of a chamber having an inert atmosphere.

A still further objective has been to provide such a device with a minimum of potential for damaging the tin foil packet encapsulating the powdered metal sample.

These and other objectives of the invention have been attained by a mold having a generally cylindrical internal cavity. The cavity is accessible through a tapered throat region at the top of the mold. The mold is preferably constructed of an upper section removably mounted atop a base. A foil sheet is placed into the tapered throat region of the upper section of the mold and is then pressed into place within the cavity by indenting a central region of the foil sheet with an accompanying forming wand. The foil is tamped from the throat region of the mold into the generally cylindrical cavity and the measured powdered metal sample is poured into the open upper end of the tin foil which is formed into a generally cup configuration. The diameter of the cylindrical cavity preferably corresponds to the diameter of the crucible in the oxygen analyzer, typically 0.18 inches, thereby ensuring the appropriate uniform dimension for the packet. The foil is prevented from slipping out of the cavity in the mold by an optional retaining rim projecting into the cavity from a sidewall of the mold.

Once the measured powdered metal is poured into the cup shaped tin foil sheet within the cavity of the mold, a tweezers on the accompanying wand is used to fold over the foil onto the sample and then a forming end of the wand is used to gently tamp or pack the sample into the cylindrical chamber. The sample is thereby encapsulated into a tightly formed tin foil package of the appropriate dimensions.

After the powdered metal sample is thusly packaged, the upper section of the mold is removed by the operator grasping the outer surface thereof and lifting it off of the base. The packaged powdered metal sample remains on the base and an upper section thereof is exposed once the upper section of the mold is removed. The tweezers on the wand are preferably sized to fit over the sample without crushing it. The packaged powdered metal sample is removed with the tweezers from the base for disposition to a waiting airtight container or oxygen analyzer.

With the powdered metal oxygen sampling preparation device of this invention, consistently sized samples are prepared with minimal operator time and reduced potential for damage to the tin foil packet encapsulating the sample. Variations in the oxygen analysis of the sample are reduced result of the consistently packaged powdered metal samples. Furthermore, preparation time for a single sample is reduced from approximately one minute to under ten seconds and the rejection rate of unacceptable samples drops from approximately 80% to nearly 0%.

BRIEF DESCRIPTION OF THE DRAWINGS

The objectives and features of this invention will become more readily apparent from the following detailed description taken in conjunction with the accompanying drawings in which:

FIG. 1 is a perspective view of a mold and a forming wand according to this invention;

FIG. 2 is a side elevational view of an alternative embodiment of the forming wand;

FIGS. 3-8 are sequential cross-sectional diagrammatic views of a powdered metal sample being encapsulated in a tin foil sheet with the mold and forming wand of this invention; and FIG. 9 is an alternative embodiment of the mold according to this invention.

DETAILED DESCRIPTION OF THE INVENTION

A mold 10 according to this invention is shown in FIG. 1 as being generally cylindrical and having an upper section 12 adapted to be situated atop a base 14. In a preferred embodiment, the upper section 12 is approximately one inch in diameter and one inch in height. On the top surface of the upper portion is a tapered throat region 16 which provides access to a central borehole cavity 18 in the upper section 12 (FIGS. 3-8). The throat region 16 is preferably tapered at a 45° angle. The dimensions of the central cavity 18 are an important feature of this invention in order to prepare an appropriately sized powdered metal sample 20 to fit within the oxygen analyzer (not shown). An analyzer for determining the oxygen content of a prepared sample as described herein is commercially available from the Leco Corporation. For such an analyzer, the central cavity 18 in the upper section 12 of the mold 10 is dimensioned to have a maximum diameter of 0.180 inches, preferably about 0.173 inches in diameter, and approximately 0.2 inches in height.

In this preferred embodiment of the upper section 12, a socket 22, preferably 0.375 inches in diameter and approximately 0.14 inches deep, is formed in the bottom side thereof. The socket 22 is formed to accept a circular flange 24 extending upwardly from the base 14 so that the upper section 12 is nested atop the base 14 to thereby form the mold 10 of this invention. The flange 24 is provided with a generally cylindrical well 26 to cooperate with the cavity 18 in the upper section 12 when the base 14 and upper section 12 are coupled together as shown in FIGS. 3-6. The dimensions of the well 26 are preferably compatible with those of the socket 22 and cavity 18, for example 0.18 inches in diameter and 0.14 inches in height. The oversized outer diameter of the base 14 is preferably about 1.25 inches.

To assist the operator in handling the mold 10, outer side surfaces 28 and 30 respectively, of the base 14 and of the upper section 12 are preferably knurled so that they may be more easily grasped and handled by the operator. As seen in FIG. 1, the upper section 12 and the base 14 may be secured together by a chain 31. As shown in FIGS. 3-7, an optional retaining rim 32 can be formed to project inwardly from an interior sidewall of the upper section 12 into the cavity 18. The rim 32 is preferably approximately 0.025 inches in width.

A forming wand 34 as shown in FIG. 1 has an integral tweezers 36 with a pair of spaced arms 38, 38 formed at one end. The spacing between the arms 38, 38 is preferably about 0.18 inches in order to grasp the sample 20 packaged in the mold 10 without crushing it, The terminal end of each arm 38 is generally blunt. On an opposite end of the wand 34 from the tweezers 36, a rounded head 40 is formed at the outboard end of a reduced diameter elongated stem 41 for tamping or packing the tin foil sheet and powdered metal while encapsulating the sample 20. The overall length of the forming wand 34 is preferably approximately 5 inches and the diameter of the rounded head 40 is preferably about 0.11 inches.

An alternative embodiment of the forming wand 42 is shown in FIG. 2, which embodiment also includes a tweezers 44 and a rounded head 46. In this embodiment, the terminal end of each arm 48 of the tweezers is tapered in order to facilitate easier handling and manipulation of the powdered metal sample 20; however, the operator must be careful not to tear or rip the sample 20 with the tapered tweezers arm ends 48. Once again, the spacing between the arms 48 of the tweezers 44 on the accompanying forming wand 42 of this invention is preferably sized at about 0.18 inches to accommodate the prepared package 20 therein without crushing, deforming or damaging it. A thickness t of the forming wand 42 in FIG. 2 is approximately 0.3 inches.

An alternative embodiment of a mold 49 according to this invention is shown in FIG. 9 and includes a disk-shaped mount 50 positioned below a base 52 in order to provide added stability to the mold 10. The mount 50 is preferably approximately ¼ inch thick and 4 inches in diameter. A pedestal 54 on the base 52 of this embodiment is solid and does not include the well; therefore, the upper surface of the pedestal 54 forms the bottom of a cavity 55 when an upper portion or collar 56 surrounds the pedestal 54 to form the mold 49 in which the powdered metal sample 20 is prepared. A chain 57 is secured at each end thereof to the upper portion or collar 56 and the base 52, respectively, so that when the operator removes the upper portion 56 from the base 52, it is not misplaced nor lost and is readily available.

The preparation of the powdered metal sample 20 for oxygen analysis is shown sequentially in FIGS. 3-8. A foil sheet 58, preferably tin, is placed in the tapered throat region 16 of the upper section 12 of the mold 10. The foil sheet 58 is approximately 1 inch long by 0.5 inches wide and 0.0005 inches thick. The foil sheet 58 is then pressed into place with the rounded forming end 40 of the accompanying wand 34 by indenting the central region of the sheet approximately 1/16 inch. Once the foil sheet 58 is indented, the measured powdered metal sample 20 is deposited by the operator onto the cup-shaped foil sheet 58 as shown in FIG. 3. Typically, 0.2 grams of the powdered metal is used; however, this invention is useful for preparing samples for oxygen analyzers requiring other sample sizes depending upon the requirements of the specific oxygen analyzer used. In that the powdered metal tends to oxidize, this process must be done in an inert atmosphere. Therefore, the mold 10 and encapsulation process is often located in a glove box (not shown) containing an inert atmosphere such as argon in which the operator performs the encapsulating procedure with rubber gloves (not shown) as previously described.

Once the measured powdered metal sample 20 is deposited onto the indented tin foil sheet 58, the rounded head 40 of the forming wand 34 is used to tamp and compact the sample 20 into the cavity 18 of the mold 10 as shown in FIG. 4. During this process, the retaining rim 32 projecting from the interior sidewall of the upper section 12 of the mold 10 is helpful to retain the tin foil 58 within the cavity 18; however, the operator must be careful not to tear the tin foil 58 on the retaining rim 32.

The powdered metal sample 20 is then encapsulated with the tin foil sheet 58 by using either the tweezers 36 or the rounded forming end 40 to work around the edges of the foil 58 by crushing the sides and folding the edges over onto the sample 20 as shown in FIGS. 5 and 6. When the sample 20 is encapsulated in the foil 58 to form a tightly packed package, the operator removes the upper section 12 of the mold 10 from the base 14 thereby exposing the sample 20 positioned within the well 26 of the base 14 as shown in FIG. 7. The diameter of the cavity 18 in the mold 10 according to this invention is sized to correspond to the crucible in the test apparatus. For example, sample 20 should be of a size no larger than 0.18 inches in diameter by 0.36 inches in length.

Alternatively, with the embodiment shown in FIG. 9, the package 20, after being formed in the manner described in connection with the embodiment of FIGS. 3-8, is positioned atop the pedestal 54 of the base 52, following which the upper section 55 is removed from the pedestal 54. The operator then easily accesses the packaged powdered metal sample 20 with the tweezers 36 on the wand 34 and removes the sample 20 from the mold 49 for disposition to a waiting airtight container or test apparatus.

A powdered metal sample is thusly prepared with the mold and forming wand of this invention for consistent oxygen analysis test results with almost a zero percent rejection rate and could be accomplished by an experienced operator in approximately 10 seconds.

From the above disclosure of the general principles of the present invention the preceding detailed description of preferred embodiments, those skilled in the art will readily comprehend the various modifications to which the present invention is susceptible. It will be appreciated that although preferred embodiments are described herein with specific sizes, masses and dimensions, these and other features can be varied within the scope of this invention to accommodate specific analyzers or applications. Therefore, I desire to be limited only by the scope of the following claims and equivalents thereof.

I claim:

1. An apparatus for preparing a powdered metal sample for analysis, the apparatus comprising:
   a mold having a cavity, said cavity being accessible via a throat region of said mold located above and in communication with said cavity, said throat region having an upper end which communicates with the upper exterior surface of the mold and being tapered downwardly and inwardly with respect to said upper exterior surface; and
   a flexible sheet positioned in said throat region and adapted to receive a powdered metal sample deposited onto said sheet, said cavity being configured for folding said sheet around the powdered metal sample therein.

2. The apparatus of claim 1 wherein said cavity is generally cylindrical.

3. The apparatus of claim 1 in combination with:
   a combination tweezers and tamping tool having a first end for tamping said sheet and sample into said cavity and a second end with a pair of prongs for folding said sheet around the powdered metal sample to form a packaged sample and for removing said packaged sample from said mold.

4. The apparatus of claim 3 wherein said first end of said tweezers is rounded to avoid tearing said sheet.

5. The apparatus of claim 1 wherein said mold comprises an upper section and a base, said upper section being removably situated atop said base to thereby provide greater access for removal of said packaged sample from said mold cavity when said upper section is removed from said base.

6. The apparatus of claim 5 further comprising:
   a socket formed in the lower region of said upper section of said mold; and
   a flange projecting upwardly from said base, said flange mating telescopingly with said socket when said upper section is situated atop said base.

7. The apparatus of claim 6 further comprising:
   a well within said flange and a bore within said upper section, said well and base cooperating with said upper section to form said cavity when said upper section is situated in telescoping relation to said base.

8. The apparatus of claim 6 wherein an upper surface of said flange underlies said cavity to form the bottom surface thereof when said upper section is situated atop said base.

9. The apparatus of claim 1 further comprising:
   a rim projecting inwardly into said cavity from a sidewall of said mold for retaining said foil sheet and said sample within said cavity.

10. The apparatus of claim 1 wherein said mold has an exterior side surface which is knurled to provide for easier handling of said mold by an operator.

11. The apparatus of claim 1 further comprising:
    a mount positioned below said mold to provide stability to said mold during the packaging of the sample.

12. The apparatus of claim 1 wherein said powdered metal sample weighs about 0.2 grams.

13. A method for preparing a powdered metal sample for analysis comprising:
    placing a flexible sheet in a throat region of a mold, said throat region providing access to a cavity in said mold;
    depositing the sample onto said sheet;
    tamping said sheet with the sample thereon into said cavity of said mold;
    folding said sheet around the sample; and
    removing said folded sheet and the sample conformed therein from said mold.

14. The method of claim 13 further comprising:
    indenting said sheet in a central region thereof prior to depositing the sample thereon.

15. The method of claim 13 further comprising:
    temporarily retaining said sheet and the sample within said cavity below a rim projecting inwardly into said cavity from a sidewall of said mold.

16. The method of claim 13 further comprising:
    measuring a desired amount of the powdered metal to establish the sample prior to said depositing step.

17. The method of claim 16 wherein said desired amount is about 0.2 grams.

18. A method for preparing a powdered metal sample for analysis comprising:
    placing a flexible sheet in a throat region of a mold, said throat region providing access to a cavity in said mold located below said throat region, said mold having an upper section and a base;
    depositing the sample onto said sheet;
    tamping said sheet with the sample thereon into said cavity of said mold;
    folding said sheet around the tamped sample;

removing said upper portion of said mold from said base to thereby expose said folded sheet with sample contained therein positioned on said base; and
removing said folded sheet and the sample contained therein from said base.

19. The method of claim 18 further comprising:
indenting said sheet in a central region thereof prior to depositing the sample thereon.

20. The method of claim 18 further comprising:
temporarily retaining said sheet and the sample within said cavity below a rim projecting inwardly into said cavity from a sidewall of said mold.

21. The method of claim 18 further comprising:
measuring a desired amount of the powdered metal to establish the sample prior to said depositing step.

22. The method of claim 21 wherein said desired amount of the powdered metal is about 0.2 grams.

23. A method for preparing a powdered metal sample for analysis comprising:
placing a flexible sheet in a throat region of a mold, said throat region being tapered with respect to an upper edge of said mold and providing access to a cavity in said mold located below said throat region;
depositing the sample onto said sheet;
tamping said sheet supported sample into said cavity of said mold;
folding said sheet around the sample; and
removing said sheet and the sample contained therein from said mold.

24. The method of claim 23 further comprising:
indenting said sheet in a central region thereof prior to depositing the sample thereon.

25. The method of claim 23 further comprising:
temporarily retaining said sheet and the sample within said cavity below a rim projecting inwardly into said cavity from a sidewall of said mold.

26. The method of claim 23 further comprising:
measuring a desired amount of the powdered metal to establish the sample prior to said depositing step.

27. The method of claim 26 wherein said desired amount of the powdered metal is about 0.2 grams.

* * * * *